(12) United States Patent
Dublin et al.

(10) Patent No.: US 7,319,901 B2
(45) Date of Patent: Jan. 15, 2008

(54) OPTIONAL TELEMETRY ANTENNA FOR IMPLANTABLE MEDICAL DEVICES

(75) Inventors: Garry L. Dublin, Maple Grove, MN (US); William D. Verhoef, Andover, MN (US); Rodney S. Wallace, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 11/248,352

(22) Filed: Oct. 12, 2005

(65) Prior Publication Data

US 2006/0224207 A1  Oct. 5, 2006

Related U.S. Application Data

(63) Continuation of application No. 11/096,834, filed on Mar. 31, 2005.

(51) Int. Cl.
*A61N 1/00* (2006.01)
(52) U.S. Cl. .......................................................... 607/36
(58) Field of Classification Search .................. 607/36, 607/37, 38, 60, 32; 128/903
See application file for complete search history.

(56) References Cited

U.S. PATENT DOCUMENTS

| | | | | |
|---|---|---|---|---|
| 5,861,019 A | * | 1/1999 | Sun et al. ...................... | 607/60 |
| 6,167,312 A | * | 12/2000 | Goedeke ...................... | 607/60 |
| 6,240,317 B1 | * | 5/2001 | Villaseca et al. .............. | 607/60 |
| 6,488,704 B1 | * | 12/2002 | Connelly et al. ........... | 623/1.15 |
| 6,505,072 B1 | * | 1/2003 | Linder et al. .................. | 607/32 |
| 6,675,045 B2 | * | 1/2004 | Mass et al. .................... | 607/32 |
| 6,708,065 B2 | * | 3/2004 | Von Arx et al. .............. | 607/60 |
| 7,149,578 B2 | * | 12/2006 | Edvardsson ................... | 607/17 |
| 2002/0065539 A1 | * | 5/2002 | Von Arx et al. .............. | 607/60 |
| 2002/0123776 A1 | * | 9/2002 | Von Arx et al. .............. | 607/60 |
| 2006/0020300 A1 | * | 1/2006 | Nghiem et al. ............... | 607/60 |
| 2006/0224207 A1 | * | 10/2006 | Dublin et al. ................. | 607/37 |

* cited by examiner

*Primary Examiner*—Carl Layno
*Assistant Examiner*—Jon-Eric C. Morales
(74) *Attorney, Agent, or Firm*—Daniel G. Chapik (57) ABSTRACT

An implantable medical device ("IMD") configured in accordance with an example embodiment of the invention generally includes a housing, a connector header block coupled to the housing, and an optional telemetry antenna coupled to the header block. The optional antenna assembly is suitably configured to support the intended IMD application (e.g., the desired telemetry range, the intended IMD implant location, or other practical considerations). The optional antenna assembly may be utilized by itself or in cooperation with a permanent telemetry antenna of the IMD. In one practical embodiment, the optional antenna assembly has a connection end that is compliant with known pacemaker electrode lead standards, which allows the IMD to leverage existing connection methodologies.

13 Claims, 7 Drawing Sheets

OPTIONAL TELEMETRY ANTENNA FOR IMPLANTABLE MEDICAL DEVICES

This application is a continuation of application Ser. No. 11/096,834, filed Mar. 31, 2005, still pending.

TECHNICAL FIELD

The present invention relates generally to implantable medical devices ("IMDs"). More particularly, the present invention relates to telemetry antennas suitable for deployment in IMDs.

BACKGROUND

The prior art is replete with a variety of IMDs that provide diagnostic and/or therapeutic capabilities. Such IMDs include, without limitation: cardiac pacemakers; implantable cardioverters/defibrillators ("ICDs"); and various tissue, organ, and nerve stimulators or sensors. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads. The header block is typically molded from a relatively hard, dielectric, non-conductive polymer having a thickness approximating the thickness of the housing. The header block includes a mounting surface that conforms to, and is mechanically affixed against, a mating sidewall surface of the housing.

It has become common to provide a communication link between the hermetically sealed electronic circuitry of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. As the technology has advanced, IMDs have become more complex in possible programmable operating modes, menus of available operating parameters, and capabilities of monitoring, which in turn increase the variety of possible physiologic conditions and electrical signals handled by the IMD. Consequently, such increasing complexity places increasing demands on the programming system.

Conventionally, the communication link between the IMD and the EMD is realized by encoded radio frequency ("RF") transmissions between an IMD telemetry antenna and transceiver and an EMD telemetry antenna and transceiver. The telemetry transmission system that evolved into current common use relies upon the generation of low amplitude magnetic fields by current oscillating in an LC circuit of an RF telemetry antenna in a transmitting mode and the sensing of currents induced by a closely spaced RF telemetry antenna in a receiving mode. Short duration bursts of the carrier frequency are transmitted in a variety of telemetry transmission formats. In some products, the RF carrier frequency is set at 175 kHz, and the prior art contains various RF telemetry antenna designs suitable for use in such applications. To support such products, the EMD is typically a programmer having a manually positioned programming head having an external RF telemetry antenna. Generally, the IMD antenna is disposed within the hermetically sealed housing; however, the typically conductive housing adversely attenuates the radiated RF field and limits the data transfer distance between the programmer head and the IMD RF telemetry antennas to a few inches. This type of system may be referred to as a "near field" telemetry system.

It has been recognized that "far field" telemetry, or telemetry over distances of a few to many meters from an IMD, would be desirable. Various attempts have been made to provide antennas with an IMD to facilitate far field telemetry. Many proposals have been advanced for eliminating conventional RF telemetry antenna designs and substituting alternative telemetry transmission systems and schemes employing far higher carrier frequencies and more complex signal coding to enhance the reliability and safety of the telemetry transmissions while increasing the data rate and allowing telemetry transmission to take place over a matter of meters rather than inches.

Telemetry antennas, whether designed for near field or far field operation, are susceptible to variations in the implanted environment (the IMD and antenna are surrounded by varying amounts of conductive body tissue when deployed). For example, a practical telemetry antenna will be designed to provide adequate gain, gain pattern, and bandwidth for the intended application. In this regard, a given antenna designed and tuned for operation with a subcutaneously implanted IMD may not perform effectively with a sub-muscularly implanted IMD (due to the increased gain requirements for a sub-muscle deployment). Furthermore, a given antenna designed and tuned for operation with a near field telemetry system may not perform effectively in a far field telemetry system. Consequently, it may be necessary for an IMD manufacturer to provide multiple versions of an IMD product, where each version has a different antenna architecture that is specifically designed to accommodate a particular implant location and/or telemetry system.

It remains desirable to provide an IMD telemetry antenna system that eliminates drawbacks associated with the IMD telemetry antennas of the prior art. In particular, it is desirable to have an interchangeable or optional telemetry antenna system for an IMD. Furthermore, other desirable features and characteristics of the present invention will become apparent from the subsequent detailed description and the appended claims, taken in conjunction with the accompanying drawings and the foregoing technical field and background.

BRIEF SUMMARY

An IMD configured in accordance with an embodiment of the invention includes an optional telemetry antenna having a connection end that is secured within the header block of the IMD. The optional telemetry antenna may be employed in addition to a "fixed" antenna element, such as an antenna element that is encapsulated within the header block, or it may serve as the only antenna element for the IMD. The specific configuration, RF characteristics, antenna gain, and other operational features of the optional antenna are selected to suit the needs of the particular IMD and/or the particular implant location. In this regard, the IMD can be outfitted with an appropriate antenna that is optimized to suit the needs of the particular IMD application, e.g., in consideration of the operating environment, the age, sex, size, or condition of the patient, or implant orientation within the patient. The optional nature of the antenna facilitates the adjustment of antenna gain to compensate for body losses based on the implant depth.

The above and other aspects of the invention may be carried out in one form by an IMD having a housing, a header block coupled to the housing, an RF module contained in the housing, and an optional antenna assembly having a connector element located within the header block and coupled to the RF module, and a free end external to the housing.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description refers to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

The invention relates to an IMD having an optional RF telemetry antenna. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna generally has two functions: to convert the electromagnetic power of a downlink telemetry transmission of an EMD telemetry antenna propagated through the atmosphere (and then through body tissues) into a UHF signal that can be processed by the IMD transceiver into commands and data that are intelligible to the IMD electronic operating system; and to convert the uplink telemetry UHF signals of the IMD transceiver electronics into electromagnetic power propagated through the body tissue and the atmosphere so that the EMD telemetry antenna or antennas can receive the signals.

Figure 1:
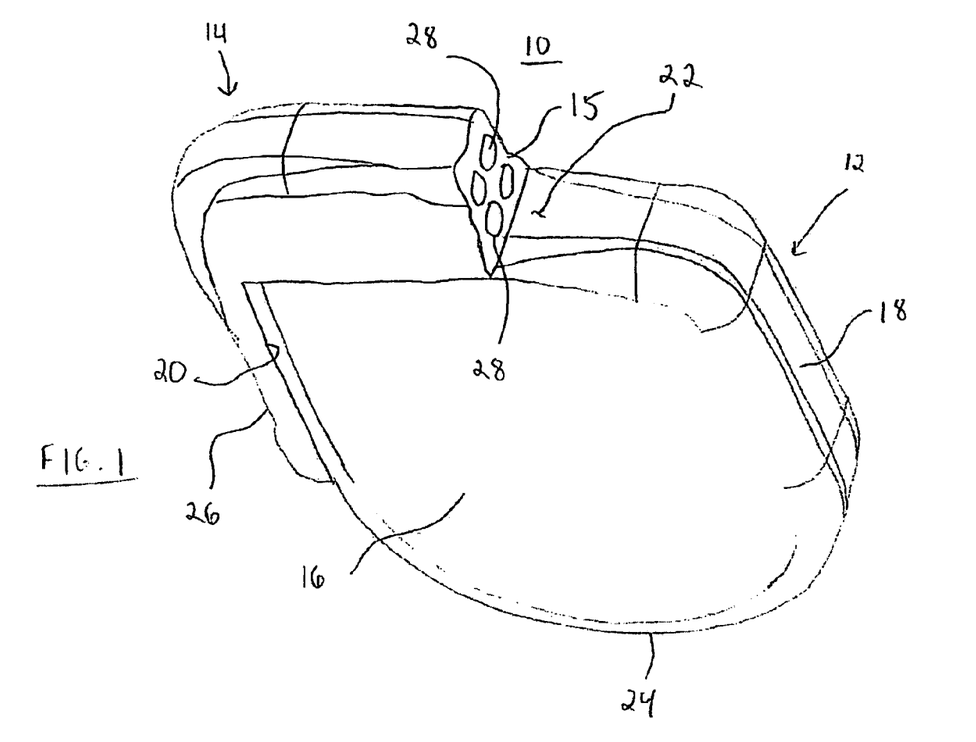
FIG. 1 is a perspective view of an IMD.

FIG. 1 is a perspective view of an IMD 10 having a hermetically sealed housing 12 and a connector header or block 14. A set of IMD leads having electrodes (such as cardioversion/defibrillation electrodes and pace/sense electrodes) disposed in operative relation to a patient's heart are adapted to be coupled to the header block 14 in a manner well known in the art. For example, such leads may enter at an end 15 of header block 14 and be physically and electrically connected to conductive receptacles, terminals, or other conductive features located within header block 14. IMD 10 is adapted to be implanted subcutaneously in the body of a patient such that it becomes encased within body tissue and fluids, which may include epidermal layers, subcutaneous fat layers, and/or muscle layers.

Hermetically sealed housing 12 is generally circular, elliptical, prismatic, or rectilinear, with substantially planar major sides (only one major side 16 is shown in FIG. 1) joined by perimeter sidewalls. The perimeter sidewalls include a substantially straight first sidewall 18, a substantially straight second sidewall 20 opposing first sidewall 18, a substantially straight upper sidewall 22, and a curvilinear lower sidewall 24 opposing upper sidewall 22. Housing 12 is typically formed from pieces of a thin-walled biocompatible metal such as titanium. Two half sections of housing 12 may be laser seam welded together using conventional techniques to form a seam extending around the perimeter sidewalls.

Housing 12 and header block 14 are often manufactured as two separate assemblies that are subsequently physically and electrically coupled together. Housing 12 may contain a number of functional elements, components, and features, including (without limitation): a battery; a high voltage output capacitor; integrated circuit ("IC") devices; a processor; memory elements; a therapy module or circuitry; an RF module or circuitry; and an antenna matching circuit. These components may be assembled in spacers and disposed within the interior cavity of housing 12 prior to seam welding of the housing halves. During the manufacturing process, electrical connections are established between components located within housing 12 and elements located within header block 14. For example, housing 12 and header block 14 may be suitably configured with IC connector pads, terminals, feedthrough elements, and other features for establishing electrical connections between the internal therapy module and the therapy lead connectors within header block 14 and for establishing connections between the internal RF module and a portion of a telemetry antenna element located within header block 14. Structures and techniques for establishing such electrical (and physical) connections are known to those skilled in the art and, therefore, will not be described in detail herein.

Header block 14 is preferably formed from a suitable dielectric material, such as a biocompatible synthetic polymer. In some embodiments, the dielectric material of header block 14 may be selected to enable the passage of RF energy that is either radiated or received by a telemetry antenna (not shown in FIG. 1) encapsulated within header block 14. The specific material for header block 14 may be chosen in response to the intended application of IMD 10, the electrical characteristics of the environment surrounding the implant location, the desired operating frequency range, the desired RF antenna range, and other practical considerations.

In accordance with one example embodiment, header block 14 is approximately one inch wide (measured along upper sidewall 22), approximately one-half inch high, and approximately one-half inch thick. It should be appreciated that the shape, size, topology, and placement of header block 14 relative to housing 12 may vary from one application to another, and that the particular configuration shown in FIG. 1 represents only one practical example. In this regard, header block 14 may, but need not, have a "tail" or "back wrap" portion 26 that extends partially down sidewall 20. Alternate embodiments may include a longer or shorter back wrap 26, depending upon the desired locations of electrical connections and interface points, or depending upon the layout and routing of conductive elements contained within header block 14 and back wrap 26. In addition, header block 14 need not be located on upper sidewall 22 (or any sidewall) and may instead be located on one of the planar major sides of housing 12. Furthermore, more than one header block 12 may be utilized in a practical implementation.

Figure 2:
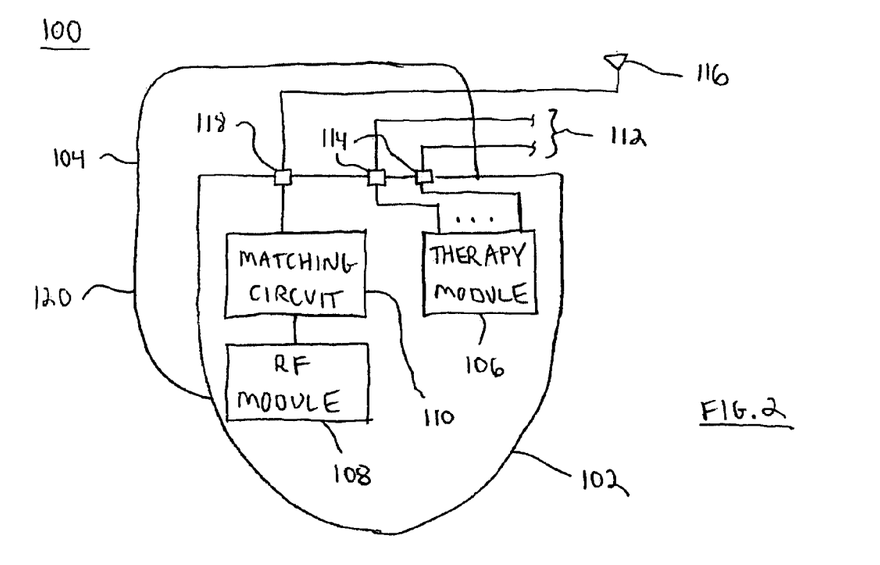
FIG. 2 is a schematic representation of an IMD and functional elements associated with the IMD.

FIG. 2 is a simplified schematic representation of an IMD 100 and several functional elements associated therewith. IMD 100 generally includes a housing 102, a header block 104 coupled to housing 102, a therapy module 106 contained within housing 102, an RF module 108 contained within housing 102, and an RF impedance matching circuit 110, which may also be contained within housing 102. Housing 102 and header block 104 may be configured as described above in connection with FIG. 1. In practice, IMD 100 will also include a number of conventional components and features necessary to support the functionality of IMD 100. Such conventional elements will not be described herein.

Therapy module 106 may include any number of components, including, without limitation: electrical devices, ICs, microprocessors, controllers, memories, power supplies, and the like. Briefly, therapy module 106 is configured to provide the desired functionality associated with the IMD 100, e.g., defibrillation pulses, pacing stimulation, patient monitoring, or the like. In this regard, therapy module 106 may be coupled to one or more therapy leads 112. In practice, the connection ends of therapy leads 112 are inserted into header block 104, where they establish electrical contact with conductive elements coupled to therapy module 106. Therapy leads 112 may be inserted into suitably configured lead bores formed within header block 104. In FIG. 1, lead bores are identified by reference number 28. In the example embodiment, IMD 100 includes feedthrough elements 114 that bridge the transition between housing 102 and header block 104. Therapy leads 112 extend from header block 104 for routing and placement within the patient.

RF module 108 may include any number of components, including, without limitation: electrical devices, ICs, amplifiers, signal generators, a receiver and a transmitter (or a transceiver), modulators, microprocessors, controllers, memories, power supplies, and the like. Although matching circuit 110 is illustrated as a separate component coupled to RF module 108, it may instead be incorporated into RF module 108 in a practical embodiment. Briefly, RF module 108 supports RF telemetry communication for IMD 100, including, without limitation: generating RF transmit energy; providing RF transmit signals to antenna 116; processing RF telemetry signals received by antenna 116, and the like. In practice, RF module 108 may be designed to leverage the conductive material used for housing 102 as an RF ground plane (for some applications), and RF module 108 may be designed in accordance with the intended application of IMD 100, the electrical characteristics of the environment surrounding the implant location, the desired operating frequency range, the desired RF antenna range, and other practical considerations.

Matching circuit 110 may include any number of components, including, without limitation: electrical components such as capacitors, resistors, or inductors; filters; baluns; tuning elements; attenuators; limiters; or the like. Matching circuit 110 is suitably configured to provide impedance matching between an optional antenna assembly 116 and RF module 108, thus improving the efficiency of antenna assembly 116. Matching circuit 110 may leverage known techniques to alter the electrical characteristics of antenna assembly 116 to suit the needs of the particular application.

Antenna assembly 116 is coupled to matching circuit 110 and/or to RF module 108 to facilitate RF telemetry between IMD 100 and an EMD (not shown). Generally, antenna assembly 116 is suitably configured for UHF or VHF operation. In the example embodiment shown in FIG. 1, a first portion of antenna assembly 116 is located within header block 104, and a second portion of antenna assembly 116 extends outside of header block 104 and outside of housing 102. In the preferred embodiment of the invention, antenna assembly 116 is an optional feature of IMD 100. Antenna assembly 116 is coupled to matching circuit 110 and/or to RF module 108 via an RF feedthrough 118, which bridges housing 102. Although not shown in FIG. 2, antenna assembly 116 may include a connection end that is coupled to RF feedthrough via a conductive terminal or feature located within header block 104. Briefly, a practical RF feedthrough 118 includes a ferrule supporting a non-conductive glass or ceramic annular insulator. The insulator supports and electrically isolates a feedthrough pin from the ferrule. During assembly of housing 102, the ferrule is welded to a suitably sized hole or opening formed in housing 102. Matching circuit 110 and/or RF module 108 is then electrically connected to the inner end of the feedthrough pin. The connection to the inner end of the feedthrough pin can be made by welding the inner end to a substrate pad, or by clipping the inner end to a cable or flex wire connector that extends to a substrate pad or connector. The outer end of the feedthrough pin serves as a connection point for antenna assembly 116, or as a connection point for an internal connection socket, terminal, or feature that receives the connection end of antenna assembly 116.

In FIG. 2, RF feedthrough 118 is located on the upper perimeter sidewall of housing 102 such that it defines a feed point for antenna assembly 116, leading from housing 102 into header block 104. Alternatively, RF feedthrough 118 may be located on the lower perimeter sidewall of housing 102, on either of the major perimeter sidewalls of housing 102, or on either of the major sides of housing 102. In an alternate embodiment described in more detail herein, RF feedthrough 118 is located on the back perimeter sidewall of housing 102, leading into the back wrap 120 of header block 104. Indeed, any of the antenna arrangements described herein may be modified to accommodate different RF feedthrough locations. For example, a given antenna assembly may utilize an input section that leads from the RF feedthrough location to the main section of the header block.

Figure 3:
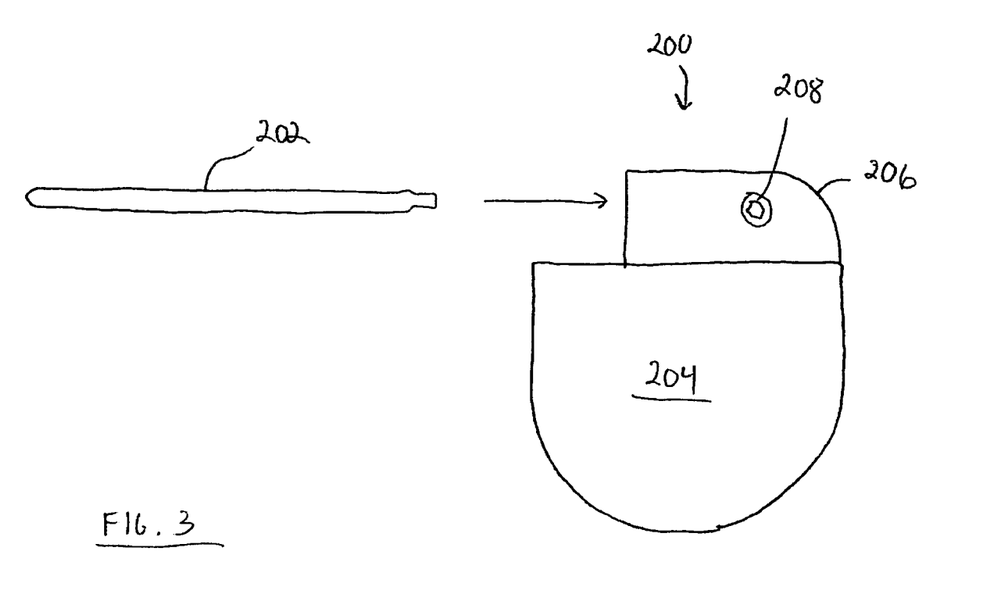
FIG. 3 is a front view of an IMD and an optional antenna assembly before installation in the IMD.

FIG. 3 is a front view of an IMD 200 and an optional antenna assembly 202. Certain features and aspects of IMD 200 are similar to those described above in connection with IMD 10 and IMD 100, and shared features and aspects will not be redundantly described in the context of IMD 200. IMD 200 generally includes a housing 204 and a header block 206 coupled to housing 202. FIG. 3 depicts IMD before installation of optional antenna assembly 202. As used herein, "optional antenna assembly" means that the antenna assembly is not manufactured as a permanent feature of the given device, and the antenna assembly is optional in that a clinician, manufacturer, or technician has the option of installing one of a plurality of available antenna assemblies (and, in some embodiments, no optional antenna assembly) to suit the needs of the particular application. In accordance with one example embodiment of the invention, optional antenna assembly 202 can be removably coupled to header block 206.

In practice, one antenna assembly may be suitably configured for far field telemetry applications, while another antenna assembly may be suitably configured for near field telemetry applications. In addition, one antenna assembly may be suitably configured for use when the IMD is implanted subcutaneously, while another antenna assembly may be suitably configured for use when the IMD is implanted sub-muscularly. Thus, for example, optional antenna assembly 202 may be configured to provide far field radiation of RF transmit energy provided by an RF module contained within housing 204, and optional antenna assembly 202 may be configured in accordance with a predetermined implant location within the patient. It should be appreciated that the specific configuration (size, shape, gain, gain pattern, and other RF characteristics) of the optional antenna assembly may vary according to any number of practical considerations other than the above examples. Ultimately, depending upon the intended application, the best antenna assembly can be selected for use with IMD 200.

Figure 4:
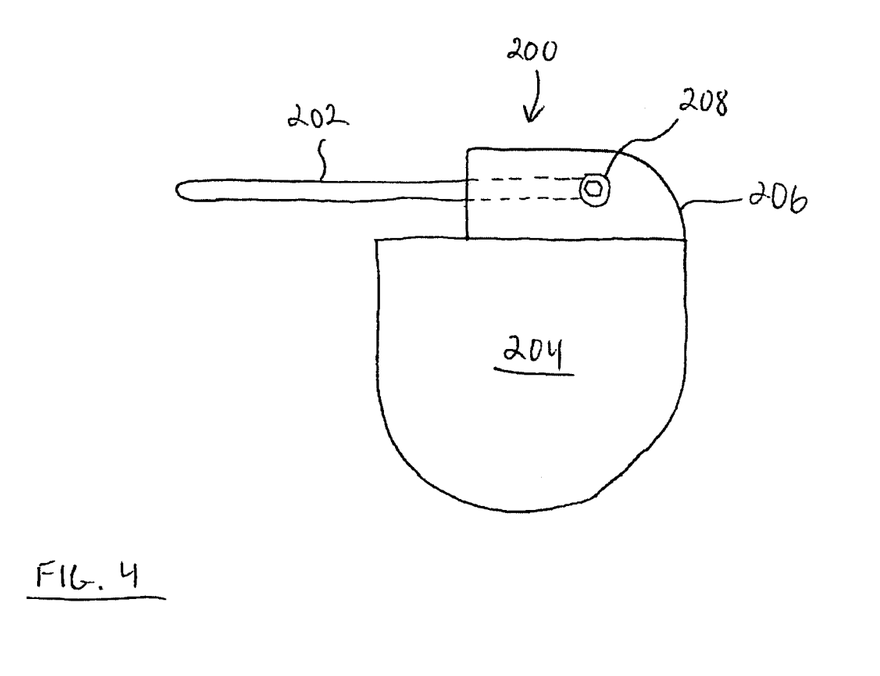
FIG. 4 is a front view of the IMD shown in FIG. 3 after installation of the optional antenna assembly.

The arrow in FIG. 3 indicates that optional antenna assembly 202 can be inserted into an appropriate receptacle, such as an antenna lead bore, formed within header block 206. In this example embodiment, header block 206 includes a set screw feature 208 that facilitates attachment of optional antenna assembly 202 to header block 206. In this regard, set screw feature 208 may function to provide physical and electrical coupling of optional antenna assembly 202. FIG. 4 is a front view of IMD 200 after installation of optional antenna assembly 202. A portion of optional antenna assembly 202 (shown in dashed lines) resides within header block 206 after installation. Set screw feature 208 is tightened to secure optional antenna assembly 202 within header block. The coupling of optional antenna assemblies within an IMD header block is described in more detail below. Those skilled in the art will recognize that IMD 200 may employ well known set screw techniques in connection with optional antenna assembly 202, including techniques commonly used for pacemaker electrode leads. Alternatively, IMD 200 may leverage other fastening methodologies and techniques, including those that do not require set screws.

Figure 5:
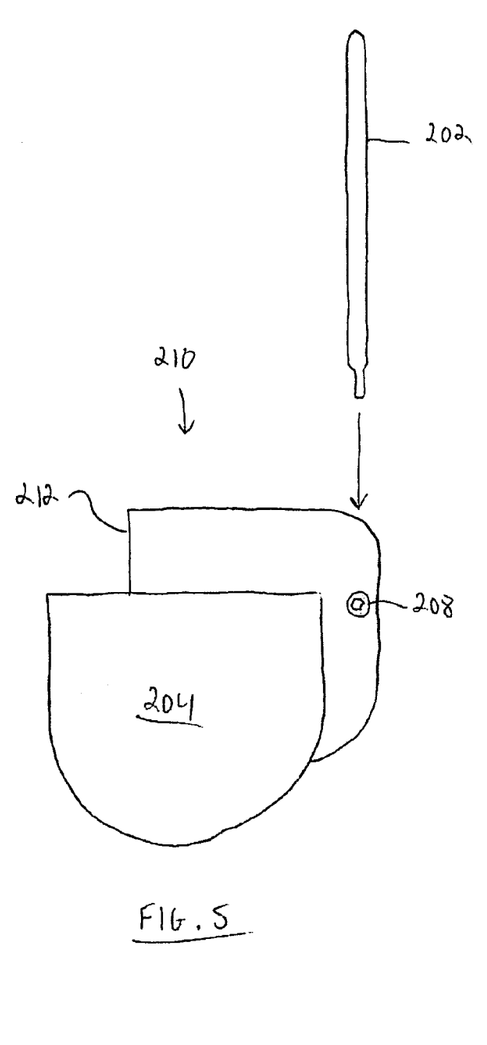
FIG. 5 is a front view of another IMD and an optional antenna assembly before installation in the IMD.
Figure 6:
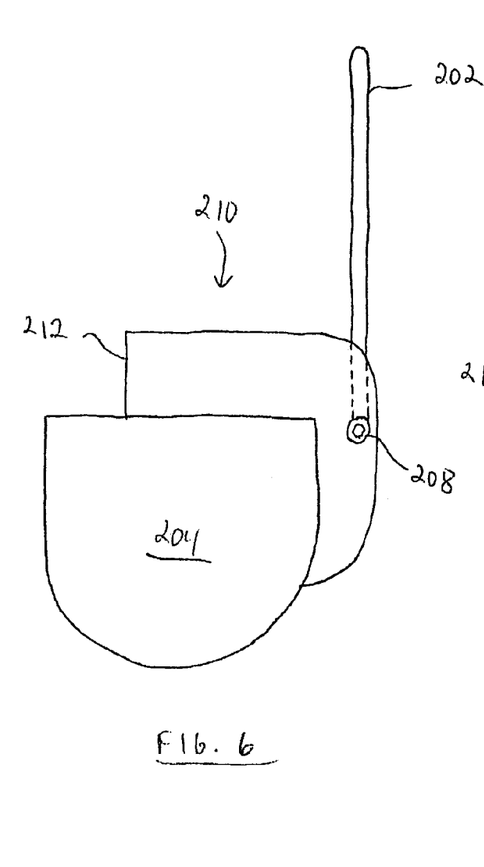
FIGS. 6 and 7 are front views of the IMD shown in FIG. 5 after installation of the optional antenna assembly.
Figure 7:
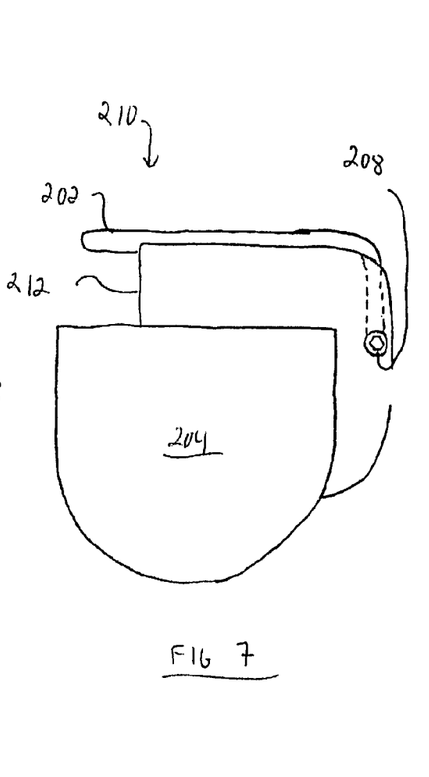

Notably, FIGS. 3 and 4 depict an embodiment where optional antenna assembly 202 enters header block 206 from the side. In practice, optional antenna assembly 202 may enter header block 206 at any suitable location. For example, FIGS. 5-7 depict another IMD 210 where optional antenna assembly 202 enters the header block 212 from the top. Certain features and aspects of IMD 210 are similar to those described above in connection with IMD 10, IMD 100, and IMD 200, and shared features and aspects will not be redundantly described in the context of IMD 210. In contrast to header block 206 utilized by IMD 200, header block 212 is configured as a back wrap header block. In further contrast to IMD 200, header block 212 may include one or more features that allow a flexible optional antenna assembly 202 to be guided around and/or secured to header block 212. For example, header block 212 may include a groove formed on its upper surface for guiding optional antenna assembly 202, tabs to provide a pressure fit securing mechanism for optional antenna assembly 202, or other elements designed to maintain optional antenna assembly 202 in a specific position or orientation, such as that shown in FIG. 7. A securing mechanism may be convenient in some applications where it would be undesirable to leave optional antenna assembly 202 "loose" within the implant site.

Figure 8:
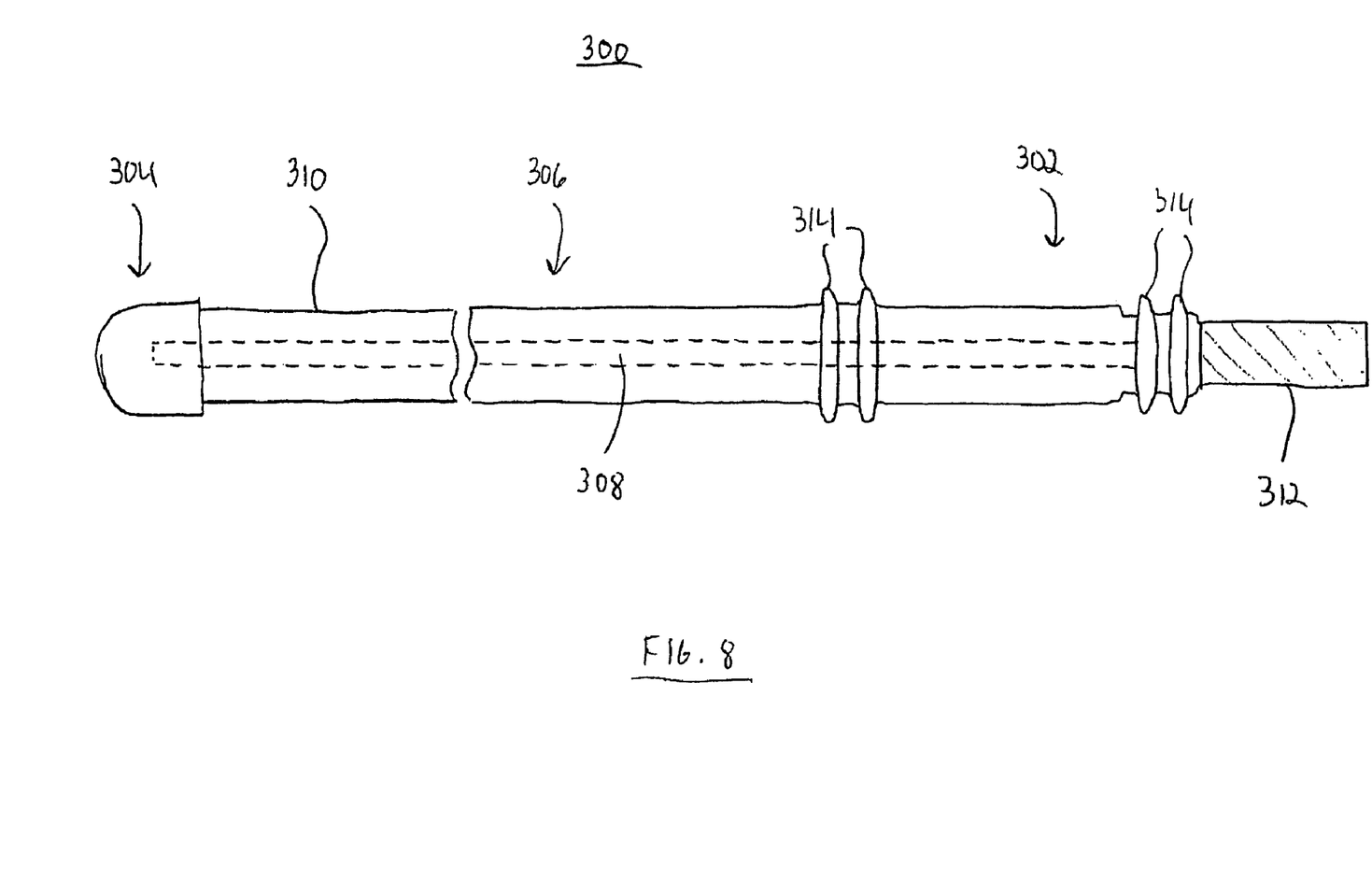
FIG. 8 is a side view of an optional antenna assembly configured in accordance with an example embodiment of the invention.
Figure 9:
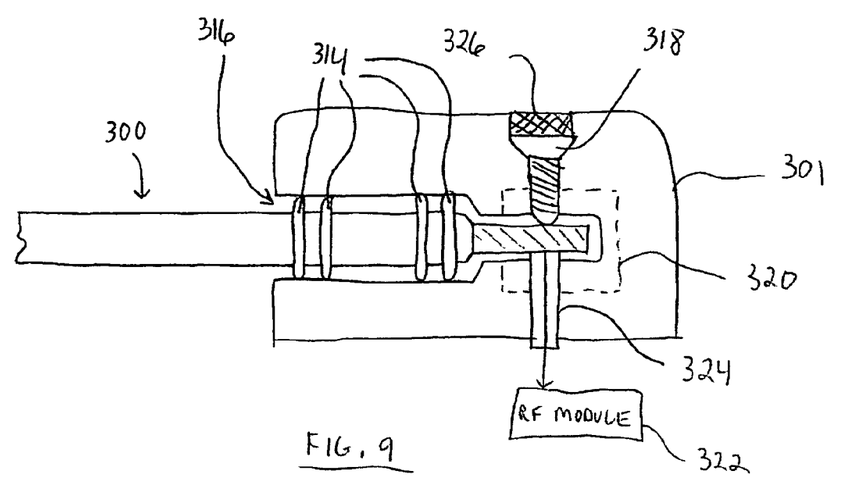
FIG. 9 is a cross sectional view of a portion of an IMD configured in accordance with an example embodiment of the invention.

FIG. 8 is a side view of an optional antenna assembly 300 configured in accordance with an example embodiment of the invention, and FIG. 9 is a cross sectional view of a portion of an IMD configured in accordance with an example embodiment of the invention. FIG. 9 depicts antenna assembly 300 installed in a header block 301 of the IMD. Antenna assembly 300 is suitable for use with any of the IMD embodiments described herein. Antenna assembly 300 generally includes a connection end 302, a free end 304, a body section 306 between connection end 302 and free end 304, an internal radiating element 308, and an external biocompatible insulator 310. Connection end 302 is suitably configured for insertion into header block 301 of a compatible IMD for purposes of establishing electrical coupling between radiating element 308 and the RF module of the IMD. In the example embodiments described herein, free end 304 is configured for deployment external to header block 301 and external to the housing of the IMD. In other words, free end 304 (and possibly a portion of body section 306) extend from header block 301, which may be desirable to provide additional antenna gain for the IMD.

Optional antenna assembly 300 includes a connector element 312 located at connection end 312. At shown in FIG. 8, connector element 312 is preferably located at the tip of antenna assembly 300. In practical embodiments, connector element 312 is formed from a biocompatible and electrically conductive material, such as niobium or titanium. As described in more detail below, connector element 312 is coupled (directly or indirectly) to radiating element 308 in a manner that facilitates the transmission of RF energy to and from the RF module in the IMD. In this regard, connector element 312 is suitably configured to establish electrical coupling with the RF module when optional antenna assembly 300 is installed in the IMD.

Biocompatible insulator 310 covers at least a portion of radiating element 308. In practice, biocompatible insulator 310 serves as the outer layer of antenna assembly 300, and it may cover all internal components of antenna assembly 300 except for connector element 312. Biocompatible insulator 310 may be formed from any suitable material, including, without limitation: silicone rubber, polyurethane, or tecothane. Depending upon the intended application, biocompatible insulator 310 may be formed from a flexible material, a rigid material, or a combination thereof, and it may be formed from a material having specific electrical characteristics or properties (e.g., dielectric constant) that enhance the RF performance of antenna assembly 300.

Antenna assembly 300 may include one or more sealing rings 314, which may be distinct elements or features incorporated into biocompatible insulator 310. As shown in FIG. 9, sealing rings 314 seal connection end 302 within an antenna lead bore 316 formed within header block 301. In practical embodiments, antenna lead bore 316 is cylindrical in shape and sealing rings 314 have a circular perimeter sized to form a contact seal with the interior surface of antenna lead bore 316. Sealing rings 314 protect the internal features of header block 310 against the ingress of body fluids when the IMD is implanted in the patient.

In the example embodiment shown herein, optional antenna assembly 300 leverages connection and sealing features that are commonly used in connection with pacemaker electrode leads. In this regard, at least a portion of antenna assembly 300 (e.g., connection end 302, and/or connector element 312) is compliant with known standards, including, without limitation: IS-TAB; IS-1, and IS-4. Likewise, header block 301 may include internal features that are compliant with such standards to ensure compatibility with connection end 302.

In practical embodiments, radiating element 308 is formed from a biocompatible conductive material, such as, without limitation: titanium alloy, niobium alloy, or the like. Radiating element 308 may be formed from a solid wire having a round cross section. In practical embodiments, radiating element 308 may be formed from a round wire having a diameter of approximately 0.020 inches. Alternatively, radiating element 308 may be formed from a hollow wire, a flat wire, a flat ribbon element, or a stamped conductor having a generally rectangular cross section (or, for that matter, any practical cross sectional shape). With brief reference to FIG. 11, the radiating element may include at least one helical section, or the entire radiating element may be helical, depending upon the specific application. The use of helical segments may be desirable to increase the effective electrical length of radiating element 308 without increasing the actual physical length of optional antenna assembly 300. Furthermore, helical segments may be desirable to facilitate impedance matching, tuning, or RF loading between antenna assembly 300 and the RF module contained in the IMD.

In accordance with one practical embodiment, an optional antenna assembly 300 having a straight wire radiating element 308 is approximately eight centimeters long. It should be appreciated that the physical length of optional antenna assembly 300, the electrical length of radiating element 308, the shape of optional antenna assembly 300, and/or other physical or electrical characteristics of optional antenna assembly 300 can vary to suit the needs of the given application. Variables to consider include, without limitation: the wavelength of the RF telemetry signals; whether the IMD supports near field or far field telemetry; the implant location for the IMD; the implant depth for the IMD; the type of IMD; the age of the patient; the size of the patient. For example, a relatively long antenna assembly 300 (having relatively more antenna gain) may be utilized for sub-muscle implantations, while a relatively short antenna assembly 300 (having relatively less antenna gain) may be utilized for subcutaneous implantations. In addition, a relatively long antenna assembly 300 may be necessary to support far field telemetry applications, while a relatively short antenna assembly 300 may be suitable to support near field telemetry applications. The optional nature of antenna assembly 300 allows a single IMD design to be deployed in multiple applications by selecting an appropriate configuration for antenna assembly 300. Indeed, in certain IMDs having permanent antenna elements, optional antenna assembly 300 need not be employed. With such applications, antenna lead bore 316 can be filled with a suitable biocompatible plug prior to implantation of the IMD.

Referring again to FIG. 9, header block 301 is configured to secure optional antenna assembly 300 within antenna lead bore 316 using a set screw feature. Although FIGS. 3-7 depict set screw features 208 that are accessible from the front of the header blocks, the set screw 318 in FIG. 9 is accessible from the top of header block 301. It should be appreciated that the specific location and access orientation of set screw 318 may vary from that shown and described herein. As mentioned above, antenna lead bore 316 is suitably sized and configured to receive optional antenna assemblies for the IMD, such as optional antenna assembly 300. An antenna terminal 320 (or equivalent structure), which is located within header block 301, is accessible via antenna lead bore 316. In FIG. 9, antenna terminal 320 is schematically represented by the dashed lines. Antenna terminal 320 is generally configured to establish electrical coupling between antenna assembly 300 and the RF module 322 in the IMD. In the example embodiment, antenna terminal 320 also establishes physical coupling between antenna assembly 300 and header block 301. As mentioned above, antenna terminal 320 may be configured to receive IS-TAB compliant optional antenna assemblies.

In the example embodiment, antenna terminal 320 includes a threaded structure supporting set screw 318, and an RF coupling element 324 that establishes RF coupling with the connector element of optional antenna assembly 300. RF coupling element 324 may be an RF feedthrough, a conductive contact pad, or the like. Set screw 318 is tightened to force the connector element of optional antenna assembly 300 against RF coupling element 324 to establish the electrical connection. In addition, the tightening of set screw 318 may serve to secure optional antenna assembly 300 within header block 301. A biocompatible seal or plug 326 covers set screw 318 to protect the internal features of header block against the ingress of body fluids after implantation of the IMD.

FIGS. 10-15 are schematic representations of IMDs configured in accordance with example embodiments of the invention. Certain features and aspects of these example IMD embodiments may be similar to those described above in connection with FIGS. 1-9, and shared features and aspects will not be redundantly described in the context of these alternate embodiments. Furthermore, for the sake of clarity, most of the internal structures of the IMDs are not shown in FIGS. 10-15.

Figure 10:
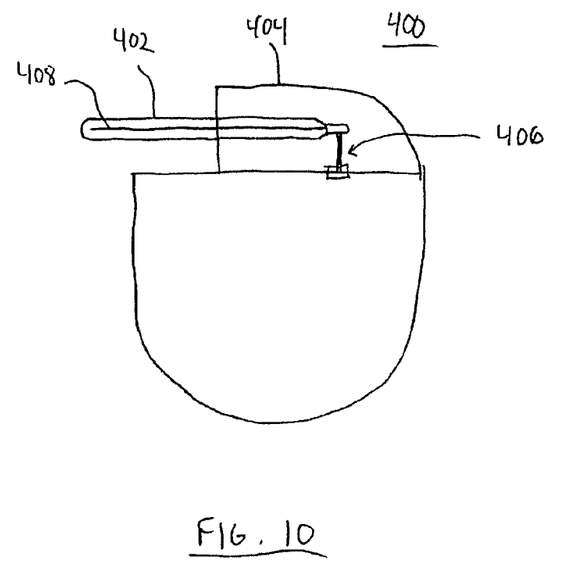
FIGS. 10-15 are schematic representations of IMDs configured in accordance with example embodiments of the invention.

FIG. 10 depicts an IMD 400 having a relatively short optional antenna assembly 402 installed in a header block 404. Notably, antenna assembly 402 is relatively short in comparison to antenna assembly 202 (see FIG. 4). Accordingly, IMD 400 may be suitable for use with relatively shallow implant depths, or suitable for use with near field telemetry applications. IMD 400 includes an RF feedthrough 406, which couples antenna assembly 402 to the RF module of IMD 400. In this example embodiment, optional antenna assembly 402 represents the only RF telemetry antenna for IMD 400. Although not required, antenna assembly 402 includes a straight radiating element 408.

Figure 11:
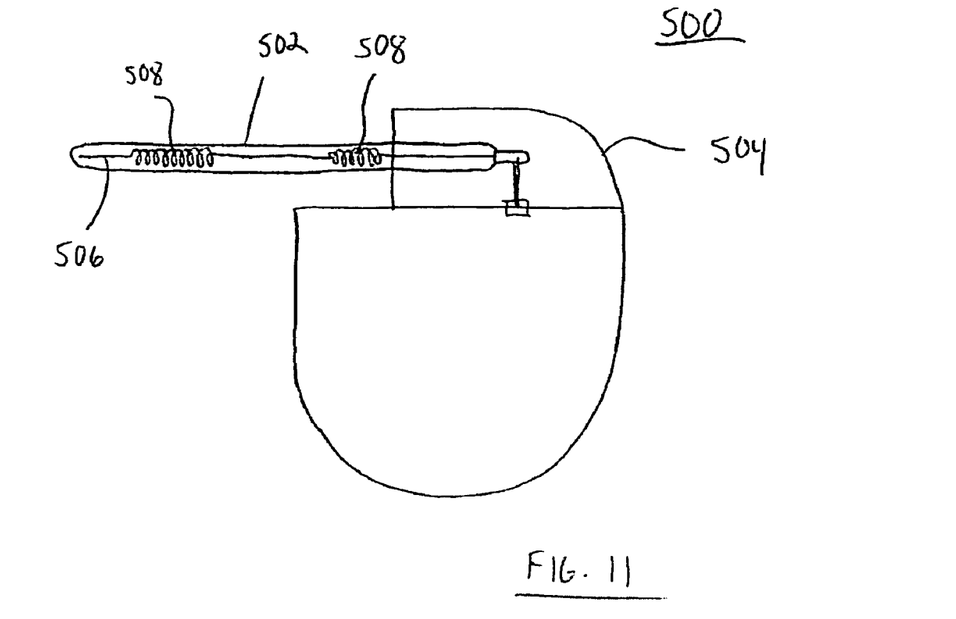

FIG. 11 depicts an IMD 500 having an optional antenna assembly 502 installed in a header block 504. In contrast to IMD 400, antenna assembly 502 incorporates a radiating element 506 having helical sections 508. As mentioned above, helical sections 508 may be utilized to increase the electrical length of antenna assembly 502 and/or to facilitate impedance matching. In this example embodiment, optional antenna assembly 502 represents the only RF telemetry antenna for IMD 500.

Figure 12:
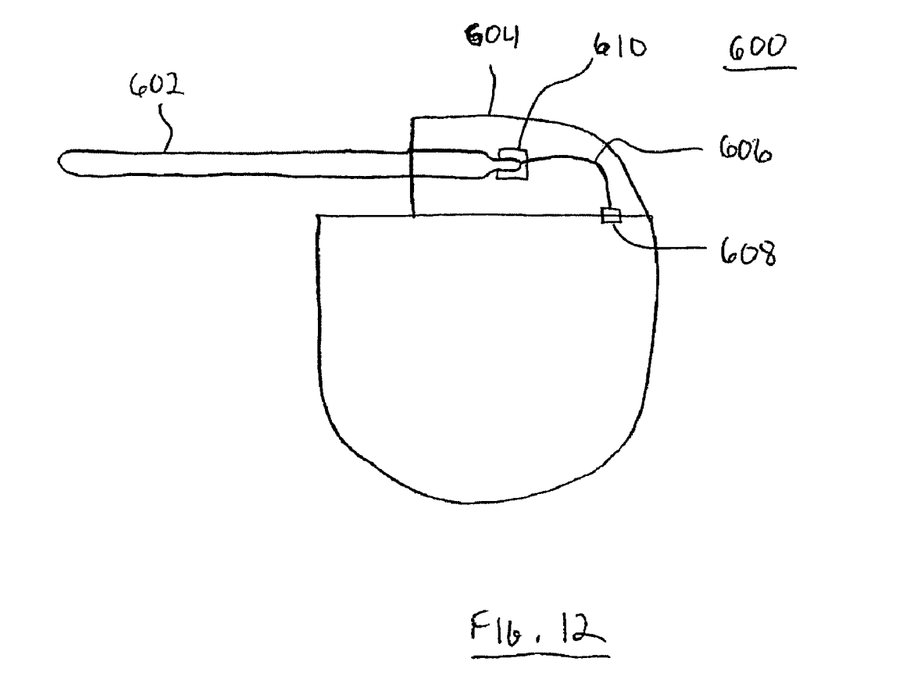

FIG. 12 depicts an IMD 600 having an optional antenna assembly 602 installed in a header block 604. Notably, IMD 600 includes a permanent antenna assembly 606 connected between the RF module (not shown) and optional antenna assembly 602. In practical embodiments, permanent antenna assembly 606 may be connected between an RF feedthrough 608, which in turn is coupled to the RF module, and an antenna terminal 610 located within header block 604. In this particular embodiment, permanent antenna assembly 606 is completely contained within header block 604. In practice, the radiating element of permanent antenna assembly 606 is encapsulated within the dielectric material that forms header block 604. Consequently, permanent antenna assembly 606 is preferably dimensioned and otherwise configured to fit within the space limitations of header block 604.

Permanent antenna assembly 606 may be dimensioned to provide far field radiation of RF transmit energy provided by the RF module contained within the IMD housing. In accordance with one practical application, permanent antenna assembly 606 is suitably dimensioned and tuned for reception and transmission of RF signals having a carrier frequency within the range of 401 MHz to 406 MHz. Permanent antenna assembly 606 may be dimensioned and tuned to account for the intended operating environment and to account for the desired operating range. Permanent antenna assembly 606 may be designed for operation by itself or configured to cooperate with optional antenna assembly 602 to provide increased antenna gain.

Permanent antenna assembly 606 may include a radiating element formed from a conductive wire, such as a titanium wire, a niobium wire, or the like. As described above in connection with FIG. 8, the radiating element for permanent antenna assembly 606 may be formed from a solid wire having a round cross section, a flat wire, a hollow wire, a flat ribbon element, or a stamped conductor having any practical cross sectional shape.

Figure 13:
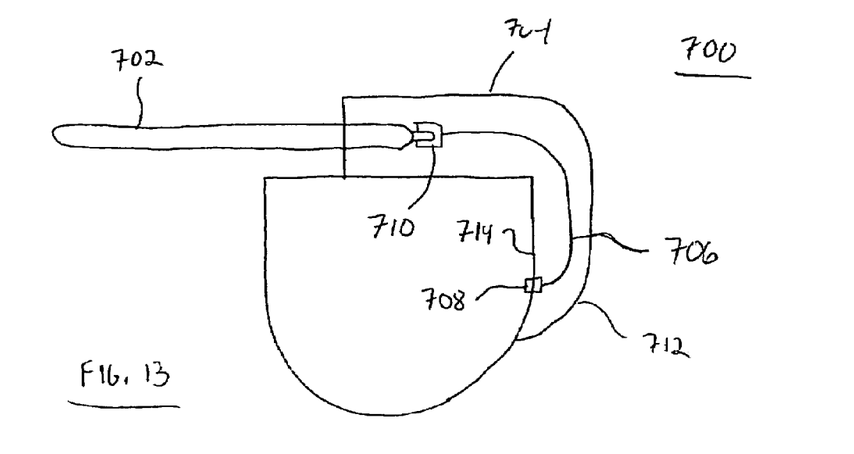

FIG. 13 depicts an IMD 700 having an optional antenna assembly 702 installed in a header block 704. IMD 700 includes a permanent antenna assembly 706 connected between the RF module (not shown) and optional antenna assembly 702. In practical embodiments, permanent antenna assembly 706 may be connected between an RF feedthrough 708, which in turn is coupled to the RF module, and an antenna terminal 710 located within header block 604. In this particular embodiment, a portion of permanent antenna assembly 706 is routed in a back wrap 712 of header block 704. Accordingly, RF feedthrough 708 is located on a major sidewall 714 of the IMD housing and permanent antenna assembly 706 may be routed along the edge of major sidewall 714 and into the upper portion of header block 704. In practice, the radiating element of permanent antenna assembly 706 is encapsulated within the dielectric material that forms header block 704 and back wrap 712. Other aspects of IMD 700 may be identical or similar to those described above in connection with IMD 600.

Figure 14:
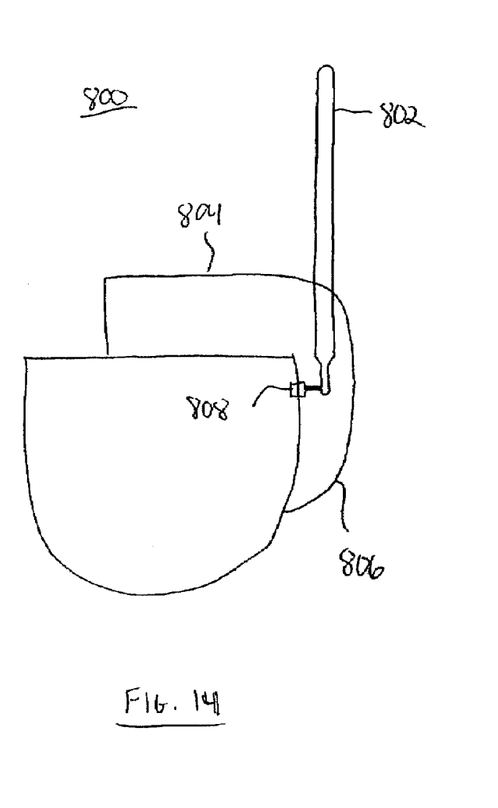

FIG. 14 depicts an IMD 800 having an optional antenna assembly 802 installed in a header block 804. In this example embodiment, header block 804 includes a back wrap 806, and antenna assembly 802 is inserted into the top of header block 804 for coupling in back wrap 806. This embodiment may be desirable to avoid extensive modifications to an existing header block design, which may include other conductive elements, set screws, lead terminals, or the like. IMD 800 includes an RF feedthrough 808, which couples optional antenna assembly 802 to the RF module of IMD 800. In this example embodiment, optional antenna assembly 802 represents the only RF telemetry antenna for IMD 800.

Figure 15:
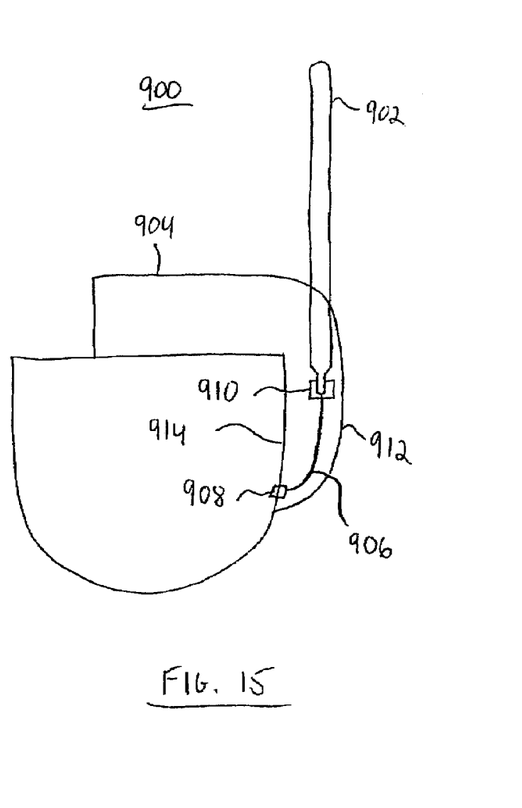

FIG. 15 depicts an IMD 900 having an optional antenna assembly 902 installed in a header block 904. In contrast to IMD 800, IMD 900 includes a permanent antenna assembly 906 connected between the RF module (not shown) and optional antenna assembly 902. In practical embodiments, permanent antenna assembly 906 may be connected between an RF feedthrough 908, which in turn is coupled to the RF module, and an antenna terminal 910 located within header block 904. In this particular embodiment, at least a portion of permanent antenna assembly 906 is routed in a back wrap 912 of header block 904. Accordingly, RF feedthrough 908 is located on a major sidewall 914 of the IMD housing and permanent antenna assembly 906 may be routed along the edge of major sidewall 914 to antenna terminal 910. In practice, the radiating element of permanent antenna assembly 906 is encapsulated within the dielectric material that forms header block 904 and back wrap 912.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

The invention claimed is:

1. An implantable medical device ("IMD") comprising:
   a housing;
   a header block coupled to said housing;
   a radio frequency ("RF") module contained in said housing, said RF module being configured to support RF telemetry for the IMD;
   an optional antenna assembly having a connector element located within said header block and coupled to said RF module, forming a free end external to said housing; and
   a permanent antenna assembly connected between said RF module and said optional antenna assembly, said optional antenna assembly being configured to cooperate with said permanent antenna assembly to provide increased antenna gain.

2. An IMD according to claim 1, at least a portion of said permanent antenna assembly being located within said header block.

3. An IMD according to claim 2, said permanent antenna assembly comprising a back wrap antenna element.

4. An IMD according to claim 1, further comprising an RF impedance matching circuit coupled to said optional antenna assembly and to said permanent antenna assembly, said RF impedance matching circuit being configured to match said optional antenna assembly and said permanent antenna assembly to said RF module.

5. An IMD according to claim 1, said optional antenna assembly being removably coupled to said header block.

6. An IMD according to claim 1, said connector element being compliant with the IS-TAB standard.

7. An IMD according to claim 1, said optional antenna assembly comprising:

a radiating element coupled to said connector element; and a biocompatible insulator covering at least a portion of said radiating element.

8. An IMD according to claim 7, said radiating element being formed from a round wire.

9. An IMD according to claim 7, said radiating element comprising at least one helical section.

10. An IMD according to claim 7, said biocompatible insulator being formed from a flexible material.

11. An IMD according to claim 7, said biocompatible insulator being formed from a rigid material.

12. An implantable medical device ("IMD") comprising:

a housing;

a header block coupled to said housing;

a radio frequency ("RF") module contained in said housing, said RF module being configured to support RF telemetry for the IMD;

an antenna lead bore formed within said header block, said antenna lead bore being configured to receive optional antenna assemblies for the IMD;

an antenna terminal located within said header block and coupled to said RF module, said antenna terminal being accessible via said antenna lead bore, said antenna terminal being configured to establish electrical coupling with optional antenna assemblies for the IMD; and a permanent antenna assembly within said header block, the permanent antenna assembly being connected between said RF module and said antenna terminal, said permanent antenna assembly being configured to cooperate with optional antenna assemblies to support RF telemetry for the IMD.

13. An IMD according to claim 12, said antenna lead bore being configured to receive optional antenna assemblies that are compliant with the IS-TAB standard, and said antenna terminal being configured to establish electrical coupling with optional antenna assemblies that are compliant with the IS-TAB standard.

* * * * *